United States Patent [19]

Baker et al.

[11] Patent Number: 5,789,630

[45] Date of Patent: Aug. 4, 1998

[54] PROCESS FOR THE SYNTHESIS OF HEXAFLUOROPROPANES

[75] Inventors: Max T. Baker; Jan A. Ruzicka, both of Iowa City, Iowa

[73] Assignee: University of Iowa Research Foundation, Iowa City, Iowa

[21] Appl. No.: 607,570

[22] Filed: Feb. 27, 1996

[51] Int. Cl.$^6$ .................................................. C07C 19/08
[52] U.S. Cl. ............................................................. 570/141
[58] Field of Search ........................................... 570/141

[56] References Cited

U.S. PATENT DOCUMENTS 2,972,639  2/1961  Stevens.

Primary Examiner—Alan Siegel
Attorney, Agent, or Firm—Charles F. Lind

[57] ABSTRACT

The invention relates to a method of synthesizing 1.1.1.3,3.3-hexafluoropropanes comprsing the additon of BrF$_3$ to malononitrile.

8 Claims, No Drawings

PROCESS FOR THE SYNTHESIS OF HEXAFLUOROPROPANES

BACKGROUND OF THE INVENTION

Compounds containing 1,1,1,3,3,3-hexafluoropropyl groups (($CF_3$)$_2CR_1R_2$) include the desirable volatile anesthetic sevoflurane ($R_1$=H, $R_2$=OCH$_2$F) and 1,1,1,3,3,3-hexafluoropropane ($R_1$=H, $R_2$=H). The basic structure of 1,1,1,3,3,3-hexafluoropropyl compounds is as follows:

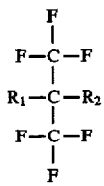

1,1,1,3,3,3-Hexafluoropropyl groups in compounds containing hexafluoropropyl groups are synthesized by various methods usually using highly toxic substances and/or involving uneconomical multiple step processes.

1,1,1,3,3,3-Hexafluoropropane may be synthesized by the reaction of malonic acid (CH2(COOH)2) with sulfur tetrafluoride (SF$_4$). This process generates undesirable intermediates and requires the use of the highly toxic sulfur tetrafluoride. The volatile anesthetic sevoflurane can be made in a process involving the reaction of (CCl$_3$)$_2$CHOCH$_3$ or (CCl$_3$)$_2$CHOCH$_2$Cl with bromine trifluoride (BrF$_3$), a process which involves multiple step chlorine replacements with fluorine (Huang and Vernice, U.S. Pat. No. 4,874,902, 1989). Chlorine replacement reactions with fluorinating agents to attain compounds with 1,1,1,3,3,3-hexafluoropropyl groups have undesirable features. Fluorochloro intermediates are formed and the yields are low. In addition, chlorine replacement reactions result in the evolution of chlorine gas (Cl$_2$). The chloro-fluoro intermediates and chlorine must be removed to obtain the final product. The purification processes increase the difficulty and cost of synthesis of 1,1,1,3,3,3-hexafluoropropyl groups. Therefore, simple and economical methods for the synthesis of 1,1,1,3,3,3-hexafluoroisopropyl compounds, which can be used to economically synthesize more complex compounds containing 1,1,1,3,3,3-hexafluoroisopropyl groups, are desirable.

SUMMARY OF THE INVENTION

This invention relates to a method of synthesizing 1,1,1,3,3,3-hexafluoropropane compounds from the compound malononitrile, a compound having the formula CH$_2$(CN)$_2$.

Another object of this invention is to provide a method for synthesizing the compound 2-bromo-1,1,1,3,3,3-hexafluoropropane from the compound malononitrile.

Yet another object of the invention is to provide a method for synthesizing the compound 2,2-dibromo-1,1,1,3,3,3-hexafluoropropane from the compound malononitrile.

A more detailed object of the invention is to provide a method for synthesizing each or all of the above-identified hexafluoropropane compounds in a single step reaction involving the compound malononitrile and bromine trifluoride (BrF$_3$).

DETAILED DESCRIPTION OF THE INVENTION

The applicants discovered that the highly reactive oxidizing and fluorinating agent BrF$_3$ unexpectedly reacts with malononitrile, CH$_2$(CN)$_2$, a compound that contains two cyano (CN) groups on the same carbon, to produce 1,1,1,3,3,3-hexafluoropropane, 2-bromo-1,1,1,3,3,3-hexafluoropropane and 2,2-dibromo-1,1,1,3,3,3-hexafluoropropane in a one step process. The reaction is performed without the need of a solvent and at easily obtained and maintained temperatures. Particularly, BrF$_3$ reacts with malononitrile to form these hexafluoropropanes in the absence of a solvent, at temperatures between about 35° and 45° C., and without destruction of the molecule. BrF$_3$ also reacts with malononitrile to form these products without the formation of undesired intermediates and alternate products, and without the evolution of chlorine gas. For example, no products that contain more or less than six fluorines, or products that contain fluorines at positions other than at the 1 and 3 carbons are formed.

EXAMPLE 1

Solid malononitrile, CH$_2$(CN)$_2$, (0.75 g) is placed in a 100 ml glass flask. The vessel is sealed other than an outlet connected to a dry-ice trap for collecting effluent vapors. The reaction vessel is placed in a water bath maintained approximately between 35° and 45° C. for liquifying the malononitrile, and the malononitrile stirred with a magnetic stirrer. No solvent is added to the malononitrile. Bromine trifluoride in liquid form with no solvent added, is slowly and continuously added via a teflon tube to the reaction flask. A slow rate of addition of BrF$_3$ is preferred to minimize the occurrence of a vigorous reaction. Gaseous products are produced and collected from the outlet in the cold trap. Following completion of the reaction as determined by the cessation of gas evolution because of depletion of malononitrile, analysis of the collected products by flame ionization gas chromatography showed that it contained three products. The three products were analyzed by gas chromatography/mass spectrometry and determined to be:

1) 1,1,1,3,3,3-Hexafluoropropane, a compound having the formula CF$_3$CH$_2$CF$_3$ [m/z (EI) 151 (M$^+$–H), 133 (M$^+$–F), 113 (C$_3$HF$_4^+$), 69 (CF3$^+$)]

2) 2-Bromo-1,1,1,3,3,3-hexafluoropropane, a compound having the formula CF$_3$CHBrCF$_3$ [m/z (EI) 230,232 (M$^+$), 211,213 (M$^+$–F), 151 (M$^+$–Br), 113 (C$_3$HF$_4^+$), 69 (CF$_3^+$)]

3) 2,2-Dibromo-1,1,1,3,3,3-hexafluoropropane, a compound having the formula CF$_3$CBr$_2$CF$_3$ [m/z (EI) 308,310, 312 (M$^+$), 229, 231 (M$^+$–Br), 210,212 (M$^+$–BrF), 113 (C$_3$HF$_4^+$), 69 (CF$_3^+$)]

EXAMPLE 2

Malononitrile, CH$_2$(CN)$_2$, (0.87 g; 13.17 mmoles), was placed in a glass reaction vessel fitted with an outlet connected to a liquid nitrogen trap for collecting effluent vapors. The reaction vessel was placed in a water bath maintained between approximately 35° and 45° C., and the malononitrile when liquified was stirred with a magnetic stirrer. Pure bromine (Br$_2$, 3.9 mmoles) in liquid form was added to serve as a moderator of the reaction. Bromine trifluoride (BrF$_3$) in a 50 μl aliquot was initially added to the reaction vessel. Additional BrF$_3$ in 100 μl portions was slowly added until a total of 1.6 ml BrF$_3$ (33.6 mmoles) had been added. The addition of BrF$_3$ was slow over 4 hours for minimizing the occurrence of a vigorous reaction. The products were collected as in Example 1. When the reaction was concluded, a small amount of bromine collected in the trap was removed with 10% aqueous sodium sulfite. The products were allowed to return to the gaseous phase upon opening and warming of the cold-trap. It was determined that a total of 210 ml of gaseous product (71% yield) were collected in the cold trap. Analysis of the collected products by flame ionization gas chromatography showed that it contained three products, identified below as 1, 2, and 3, in the percentages also indicated below:

1) 1,1,1,3,3,3-Hexafluoropropane ($CH_2(CF_3)_2$) 85–87%
2) 2-Bromo-1,1,1,3,3,3-hexafluoropropane ($CHBr(CF_3)_2$) 9%
3) 2,2-Dibromo-1,1,1,3,3,3-hexafluoropropane ($CBr_2(CF_3)_2$) 1%

The reaction of this invention, yielding the three products identified above, is shown below:

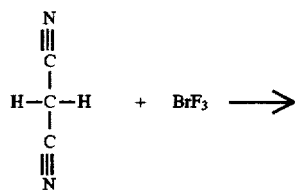

Malononitrile

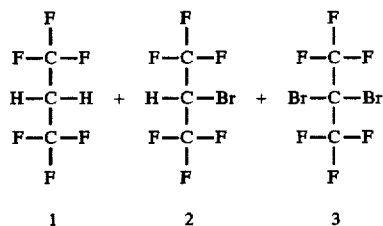

1  2  3

Each synthesized 1,1,1,3,3,3-hexafluoropropane can be purified by common practice, such as by fractional distillation, and further utilized in the economical synthesis of other compounds containing 1,1,1,3,3,3-hexafluoropropyl groups.

The results of this invention are not predictable because more commonly $BrF_3$ will react with an organic molecule not to result in fluorination of that molecule, but the destruction of that molecule. It is not predictable that an organic molecule containing two cyano groups on the same carbon will be converted to a 1,1,1,3,3,3-hexafluoropropyl group when reacted with $BrF_3$, nor is it predictable that an organic molecule containing two cyano groups on the same carbon will react with $BrF_3$ to form a 1,1,1,3,3,3-hexafluoropropane in the absence of a solvent.

Further, it is not predictable that the brominated compounds 2-bromo-1,1,1,3,3,3-hexafluoropropane or 2,2-dibromo-1,1,1,3,3,3-hexafluoropropane will be formed when malononitrile is reacted with $BrF_3$. A $BrF_3$ reaction is only known to add bromine to an unsaturated carbon-carbon bond, a double bond (C=C) (Lo et al, *J. Org. Chem.* 35:2051–2053, 1970). It is not known that $BrF_3$ reaction with a saturated organic compound, a compound with only single carbon-carbon bonds (C—C), will result in bromination of that compound. Therefore, it is not expected that reaction of $BrF_3$ with malononitrile will result in the addition of bromine to malononitrile.

What is claimed is:

1. A method of synthesizing 1,1,1,3,3,3-hexafluoropropanes, including one or more of 1,1,1,3,3,3-hexafluoropropane, 2-bromo-1,1,1,3,3,3-hexafluoropropane, or 2,2-dibromo-1,1,1,3,3,3-hexafluoropropane, comprising the addition of $BrF_3$ to malononitrile in the absence of a solvent and at a temperature between approximately 35° and 45° C.

2. A method of synthesizing a 1,1,1,3,3,3-hexafluoropropane according to claim 1, further comprising the addition of bromine trifluoride to malononitrile being in a sealed vessel fitted with an outlet to collect the products.

3. A method of synthesizing any or all of 1,1,1,3,3,3-hexafluoropropane, 2-bromo-1,1,1,3,3,3-hexafluoropropane, and 2,2-dibromo-1,1,1,3,3,3-hexafluoropropane, comprising the addition of bromine trifluoride to malononitrile in a sealed vessel fitted with an outlet to collect the products, and holding the vessel at temperatures between approximately 35 degrees C. and 45 degrees C., the method proceeding in the absence of a solvent.

4. A method of synthesizing any or all of the 1,1,1,3,3,3-hexafluoropropanes according to claim 3, further comprising the addition of $BrF_3$ to malononitrile being preceded by the addition of pure bromine to the malononitrile.

5. A method of synthesizing 1,1,1,3,3,3-hexafluoropropanes, including one or more of 1,1,1,3,3,3-hexafluoropropane, 2-bromo-1,1,1,3,3,3-hexafluoropropane, or 2,2-dibromo-1,1,1,3,3,3-hexafluoropropane, comprising the addition of bromine trifluoride to malononitrile, and further comprising the addition of bromine trifluoride to malononitrile being preceded by the addition of pure bromine to the malononitrile.

6. A method of synthesizing a 1,1,1,3,3,3-hexafluoropropane according to claim 5, further comprising the addition of bromine trifluoride to malononitrile being in the absence of a solvent.

7. A method of synthesizing a 1,1,1,3,3,3-hexafluoropropane, according to claim 5, further comprising the addition of bromine trifluoride to malononitrile being at temperatures between approximately 35 degrees C. and 45 degrees C.

8. A method of synthesizing a 1,1,1,3,3,3-hexafluoropropane according to claim 5, further comprising the addition of bromine trifluoride to malononitrile being in a sealed vessel fitted with an outlet to collect the products, and the vessel being maintained at temperatures between approximately 35 degrees C. and 45 degrees C.

* * * * *